(12) United States Patent  
Fellinger et al.

(10) Patent No.: US 7,404,260 B2
(45) Date of Patent: Jul. 29, 2008

(54) GAUGE AND METHOD FOR INDICATING ONE OR MORE PROPERTIES OF A LOOSE-FILL INSULATION

(75) Inventors: Thomas J. Fellinger, Littleton, CO (US); Raymond W. Lavallee, II, Littleton, CO (US)

(73) Assignee: Johns Manville, Denver, CO (US)

( * ) Notice: Subject to any disclaimer, the term of this patent is extended or adjusted under 35 U.S.C. 154(b) by 468 days.

(21) Appl. No.: 11/272,514

(22) Filed: Nov. 10, 2005

(65) Prior Publication Data

US 2007/0113650 A1    May 24, 2007

(51) Int. Cl.
*G01B 3/22* (2006.01)
*G01N 9/00* (2006.01)

(52) U.S. Cl. .............................. 33/833; 73/32 R; 73/818
(58) Field of Classification Search ............... 33/832, 33/833, 834, 836, 542; 374/43; 73/32 R, 73/81, 818
See application file for complete search history.

(56) References Cited

U.S. PATENT DOCUMENTS

| 4,177,618 | A |   | 12/1979 | Felter |   |
|---|---|---|---|---|---|
| 4,288,925 | A | * | 9/1981 | McMurtry | ................... 33/832 |
| 4,337,666 | A |   | 7/1982 | Bhattacharyya et al. | |
| 4,712,347 | A |   | 12/1987 | Sperber | |
| 5,287,674 | A |   | 2/1994 | Sperber | |
| 5,932,811 | A | * | 8/1999 | Giebner | ....................... 73/818 |
| 6,047,518 | A |   | 4/2000 | Lytle | |
| 6,330,779 | B1 |   | 12/2001 | Kinzler | |
| 6,581,451 | B2 |   | 6/2003 | Ence et al. | |
| 2005/0055841 | A1 | * | 3/2005 | Scherzinger et al. | .......... 33/834 |
| 2005/0081604 | A1 |   | 4/2005 | O'Leary et al. | |
| 2006/0090363 | A1 | * | 5/2006 | Luner et al. | .................... 33/833 |
| 2007/0006664 | A1 | * | 1/2007 | Suda et al. | ..................... 73/818 |
| 2008/0078245 | A1 | * | 4/2008 | O'Leary et al. | ............. 73/32 R |

* cited by examiner

*Primary Examiner*—G. Bradley Bennett
(74) *Attorney, Agent, or Firm*—Robert D. Touslee

(57) ABSTRACT

A portable gauge and method are used to determine an as installed property of a loose-fill insulation in a building cavity wherein the cavity has a given depth, an open front, a rear surface, and sidewalls defined by spaced apart framing members. The gauge includes a frame for extending between and overlapping front surfaces of the framing members to position the gauge for determining an as installed property of the insulation; a plunger assembly mounted on the frame for compressing a portion of the insulation in the cavity to a compressed density sufficiently dense to prevent plunger creep and to a compressed thickness less than the as installed thickness of the insulation; and a readout assembly calibrated to indicate an as installed property of the insulation based on the compressed thickness of the insulation.

20 Claims, 3 Drawing Sheets

GAUGE AND METHOD FOR INDICATING ONE OR MORE PROPERTIES OF A LOOSE-FILL INSULATION

BACKGROUND OF THE INVENTION

The subject invention relates to a gauge and method for indicating one or more properties of a loose-fill insulation in an open-front building cavity and, in particular, to a portable gauge that provides an easy to use, reliable and accurate device and method for quickly indicating the as installed density and/or the as installed thermal, acoustical, and/or other density related property or properties of a loose-fill insulation in open-front wall, ceiling, roof, and floor cavities and/or other similar open-front building cavities.

An increasingly preferred method of installing insulation in open-front wall, ceiling, roof, and floor cavities and other similar open-front building cavities is to insulate such cavities with a loose-fill insulation such as a fiberglass based, cellulose fiber based, rock wool based, or other insulation based loose-fill insulation. Such loose-fill insulations are typically introduced into these open-front building cavities by blowing or spraying these loose-fill insulations into the cavities in the form of small discrete portions of a fibrous or other insulation material or in the form of an admixture of small discrete portions of a fibrous or other insulation material and an adhesive. To be assured that these loose-fill insulations are properly installed and meeting the specifications and performance criteria set for such applications without having to utilize excessive amounts of the loose-fill insulation to assure that such performance criteria are met, it is important to be able to determine the as installed properties of the loose-fill insulation such as but not limited to the as installed thermal rating (R-value), acoustical rating (STC), combustion rating, and/or other as installed density related property of the loose-fill insulation. Since the installer of such loose-fill insulations is typically an insulation contractor, the installer should be provided with an easy to use, reliable, and accurate device and method for quickly indicating the as installed density and/or the as installed thermal, acoustical, and/or other density related property or properties of a loose-fill insulation in an open-front building cavity.

Several types of instruments and test procedures have been developed over the years to aid installers with loose-fill insulation density measurements from which the thermal, acoustical, and other density related properties of a loose-fill insulation are determined. One existing instrument measures the pressure drop across a thickness dimension of the installed loose-fill insulation material when a controlled amount of air is allowed to flow through the insulation. The pressure drop reading is then correlated with the installed density of the insulation, which in turn is correlated to the thermal or acoustical performance of the insulation. Since three-dimensional airflow characteristics exist in this type of measurement, correlation between the pressure drop reading and the insulation density is prone to considerable error and usually requires a large amount of correlation data for various types of loose-fill insulation and proposed installed loose-fill insulation densities before the instrument can be used as a tool for verifying installed properties of a loose-fill insulation. U.S. Pat. No. 6,330,779, named inventor Keven W. Kinzler, and UK Patent Application GB 2 103 695 A, named inventor David W. Anderson et al, disclose methods of blowing loose-fill insulation into a building cavity wherein the pressure at which the insulation is delivered and a sensed back pressure, respectively, are utilized to control the amount of loose-fill insulation introduced into the building cavity.

Another method for making loose-fill insulation density measurements from which the thermal, acoustical, and other density related properties of a loose-fill insulation are determined is to physically cut out or core a measured portion of loose-fill insulation from a cavity and then, weigh the removed loose-fill insulation core sample. By knowing the sample weight and volume, the as installed density of the material can be calculated. The calculated density can then be used to determine the density related insulation properties of the installed insulation. Although this can be an accurate method of density measurement, this method requires the use of a fairly accurate electronic measurement scale (e.g. depending on the sample size, this method may require an electronic scale that measures in 0.1 to 0.001 pound increments) and is usually not accurate for spray-on loose-fill insulations with high moisture contents. In addition, since most electronic scales are relatively fragile, it is not practical to provide insulation installers with these scales for day-to-day use at job sites. U.S. Pat. No. 6,047,518, named inventor Clifton E. Lytle, discloses a method for determining the density of an installed loose-fill insulation that includes the steps of locating a container of known volume and weight in a cavity, filling the container with loose-fill insulation, and weighing the filled container.

U.S. Pat. Nos. 4,712,347 and 5,287,674, named inventor Henry V. Sperber, disclose a method for determining an appropriate amount of loose-fill insulation in a building cavity wherein a netting material overlies and encloses the front of the building cavity. With this method, when the netting bulges slightly an appropriate amount of insulation is deemed to have been received and positioned within the enclosed cavity.

Another apparatus and method for determining the density of a loose-fill insulation in an enclosed cavity is disclosed in Patent Application Publication US 2005/0081604, named inventors Robert J. O'Leary et al. This patent application publication discloses a density determining apparatus for use in determining the density of loose-fill insulation within a cavity of known depth having an inner or front side covered with a sheet or netting to contain the insulation within the cavity. The apparatus comprises a sensor that senses force or a change in force exerted on the sensor by the insulation within a cavity. When measuring the density of insulation within a cavity, the sensor is held in a substantially fixed position relative to the insulation within the cavity so that the force exerted on the sensor by the insulation filling the cavity can be measured by the sensor to determine the density of the insulation within the cavity. The apparatus must be able to repeatedly hold the sensor in the same or substantially the same fixed relative position to the insulation within each cavity tested so that when the testing procedure is repeated for a series of these cavities, the density determined by the apparatus will be reliable. To sense the force of the insulation, the sensor may be supported in a substantially fixed position within the cavity by being attached to the netting or the sheathing (FIGS. 3A and 3B) or the sensor may be supported in a substantially fixed position against (FIGS. 5, 6, 7, and 9) or relative to (FIG. 8) the netting and insulation while being located outside of the cavity.

SUMMARY OF THE INVENTION

The portable gauge of the subject invention provides a light weight, compact, easily transported and stored, easy to use, reliable and accurate device and method for use by insulation contractors to quickly determine the as installed density of a wet or dry loose-fill insulation and/or the as installed thermal, acoustical, and/or other density related physical property or properties of a wet or dry loose-fill insulation in an open-front wall, ceiling, roof, or floor cavity and in a similar open-front building cavities. For maximum thermal, acoustical and/or other desired density related performance, insulation contractors normally fill building cavities with a loose-fill insulation so that the as installed thickness of the loose-fill insulation equals or substantially equals the depth of the cavity. Accordingly, while the portable gauge of the subject invention could be calibrated to provide as installed density and/or other as installed density related property values for as installed insulation thicknesses other than standard building cavity depths, typically, the portable gauge of the subject invention will be calibrated for an as installed loose-fill insulation thickness that corresponds to one of the standard cavity depths used in the building industry. For example, in the United States building industry the most common standard cavity depths are: 3.5 inches, 5.5 inches, 7.25 inches, and 9.25 inches. The cavity depth is 3.5 inches where the framing members defining the sidewalls of the cavities are 2×4 inch framing members, 5.5 inches where the framing members defining the sidewalls of the cavities are 2×6 framing members, 7.25 inches where the framing members defining the sidewalls of the cavities are 2×8 framing members, and 9.25 inches where the framing members are 2×10 framing members.

The portable gauge of the subject invention for indicating the as installed density and/or one or more other as installed density related properties of a loose-fill insulation within an open-front building cavity includes a rigid frame, a plunger assembly, and a readout assembly. While other plunger assemblies, such as but not limited to pneumatically or hydraulically actuated plunger assemblies, may be used in the portable gauge of the subject invention, for ease of use, portability, and cost, the plunger assembly of the portable gauge of the subject invention is a spring-loaded plunger assembly. The plunger of the plunger assembly has a faceplate with a predetermined surface area for compressing that predetermined surface area of a loose-fill insulation within a cavity to a density greater than the as installed density of the loose-fill insulation and to a compressed thickness less than the as installed thickness of the loose-fill insulation. With the frame of the portable gauge pressed against the front faces of the framing members of an open-front cavity, the plunger of the plunger assembly is urged away from the frame and toward the back surface of the cavity, by a spring or other force producing mechanism, to compress a portion of the loose-fill insulation within the cavity between the plunger faceplate and the rear surface of the cavity. Upon the application of the portable gauge to the framing members of a cavity, the force exerted on the plunger by the spring or other force producing mechanism and by the plunger faceplate on the loose-fill insulation between the plunger faceplate and the rear surface of the cavity is sufficient to compress the loose-fill insulation from its as installed thickness to a lesser thickness and to compress the loose-fill insulation from its as installed density to a greater density which is sufficiently dense or compact that further compressive movement of the plunger (plunger creep) is stopped or substantially stopped. Preferably, the compressive movement of the plunger caused by the spring or other force producing mechanism and by the plunger faceplate on the loose-fill insulation between the plunger faceplate and the rear surface of the cavity is rapid and quickly compresses the loose-fill insulation from its as installed thickness to the lesser thickness and from its as installed density to the density that stops or substantially stops further compressive movement of the plunger (plunger creep). As used herein, the density of the loose-fill insulation, which stops or substantially stops further compressive movement of the plunger, is a density that stops further compressive movement of the plunger to the extent that any further compressive movement of the plunger will be minor and not materially affect the density and/or density related property reading provided by the portable gauge whereby the portable gauge will quickly provide an accurate and reliable property value. Thus, for a given as installed loose-fill insulation (fiberglass based insulation, cellulose fiber based insulation, rock wool fiber based insulation, or other insulating material based insulation), a given as installed insulation thickness (e.g. normally the cavity depth), and a given cavity depth, the compressed thickness of the loose-fill insulation between the plunger faceplate and the rear surface of the cavity will vary depending on the as installed density of the loose-fill insulation. This compressed thickness of the loose-fill insulation is correlated (typically through testing) to the as installed density of the loose-fill insulation; the as installed density of the loose-fill insulation is then correlated (typically through testing) to one or more as installed thermal, acoustical and/or some other density related properties of the loose-fill insulation to calibrate the portable gauge; and the portable gauge is provided with a scale or scales of calibrated markings, such as but not limited to bands, that provide the installer with easy to read values for the density or density related property or properties of the as installed loose-fill insulation.

The readout assembly of the portable gauge of the subject invention can be permanently calibrated for a particular loose-fill insulation (e.g. a fiberglass based insulation, a cellulose fiber based insulation, a rock wool fiber based insulation, or other insulating material based insulation), a particular as installed insulation thickness (e.g. normally the cavity depth), and a particular cavity depth (which in the United States is typically a 3.5 inch, 5.5 inch, 7.25 inch, or 9.25 inch cavity depth). However, in preferred embodiments of the invention, the readout assembly of the portable gauge of the subject invention can be adjusted to calibrate the readout assembly for different loose-fill insulations, as installed insulation thicknesses, and cavity depths.

One preferred embodiment of the portable gauge of the subject invention includes a tubular housing, a calibration cap, and a lock nut. The tubular housing and the calibration cap are threaded together so that the calibration cap can be adjusted relative to the housing by being moved in and out relative to the housing in the direction of the longitudinal axis of the plunger stem to calibrate the portable gauge for a particular loose-fill insulation and/or as installed insulation thickness. The lock nut is used to lock the calibration cap in place once the cap has been adjusted to calibrate the portable gauge for a particular loose-fill insulation and/or as installed insulation thickness (e.g. normally the cavity depth). The plunger stem of the plunger assembly is slideably received within and passes from the rear side of the gauge frame through the frame, the tubular housing, and the calibration cap.

With the portable gauge calibrated for a particular loose-fill insulation and a particular as installed insulation thickness (e.g. normally the cavity depth) and with the frame of the portable gauge held against the front faces of the framing members of the open-front cavity, the degree to which the plunger faceplate penetrates into the cavity compressing the loose-fill insulation between the faceplate and the rear surface of the cavity relates to the as installed density of the loose-fill insulation being compressed within the cavity and determines the degree to which the free end of the plunger stem extends beyond the exposed face of the calibration cap. In other words, the greater the as installed density of the loose-fill insulation being compressed by the portable gauge within a building cavity of a given depth, the less distance the plunger assembly faceplate will penetrate into the building cavity before compression of the loose-fill insulation by the plunger will stop and the more the plunger stem will extend beyond the front face of the calibration cap to indicate as installed density or other as installed density related property value of the loose fill insulation (e.g. an as installed R-value for the insulation). Preferably, the plunger stem has a scale or scales with graduated markings or bands on a portion of its free end that, with the calibration cap properly adjusted, functions with the front face (exposed face) of the calibration cap to indicate a value or values for one or more as installed loose-fill insulation properties based on the as installed density of the loose-fill insulation within a cavity being tested. The desired as installed physical property of the loose-fill insulation (e.g. density or thermal, acoustical, or other density related property) can then be easily determined by reading the appropriate marking on the graduated scale of the plunger stem relative to the front face of the calibration cap.

DESCRIPTION OF THE PREFERRED EMBODIMENTS

Figure 1:
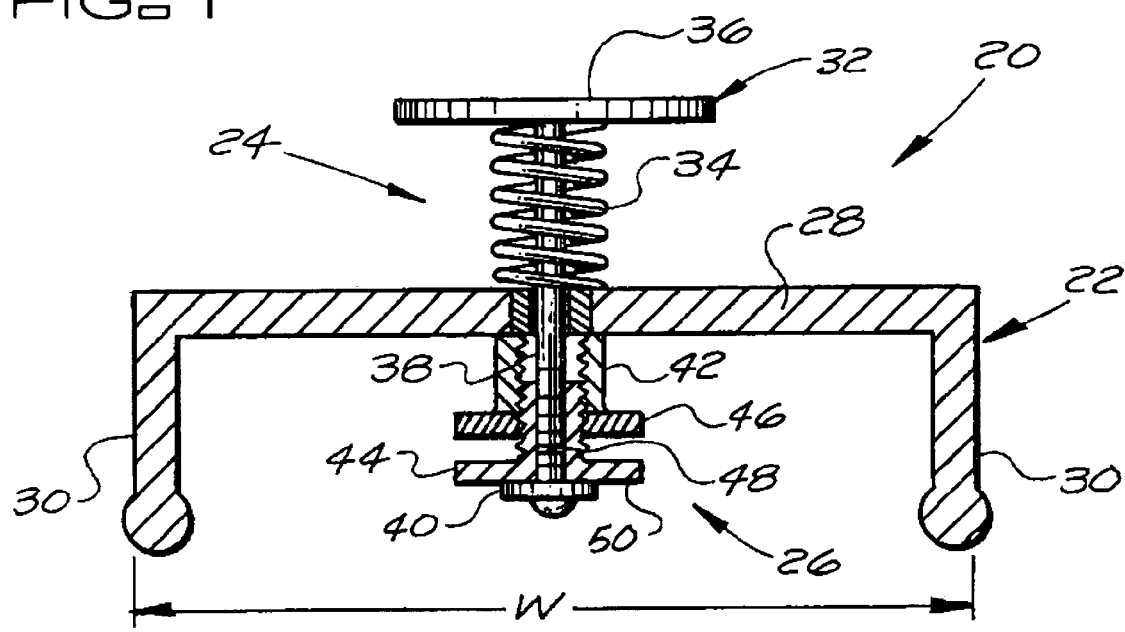
FIG. 1 is a horizontal cross section through an embodiment of the portable gauge of the subject invention.
Figure 2:
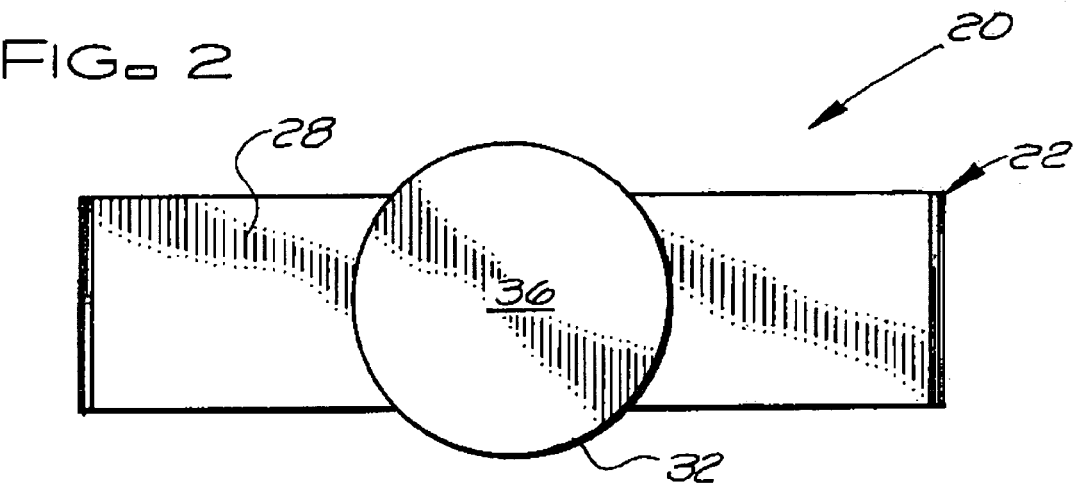
FIG. 2 is a rear view of the portable gauge of FIG. 1.
Figure 3:
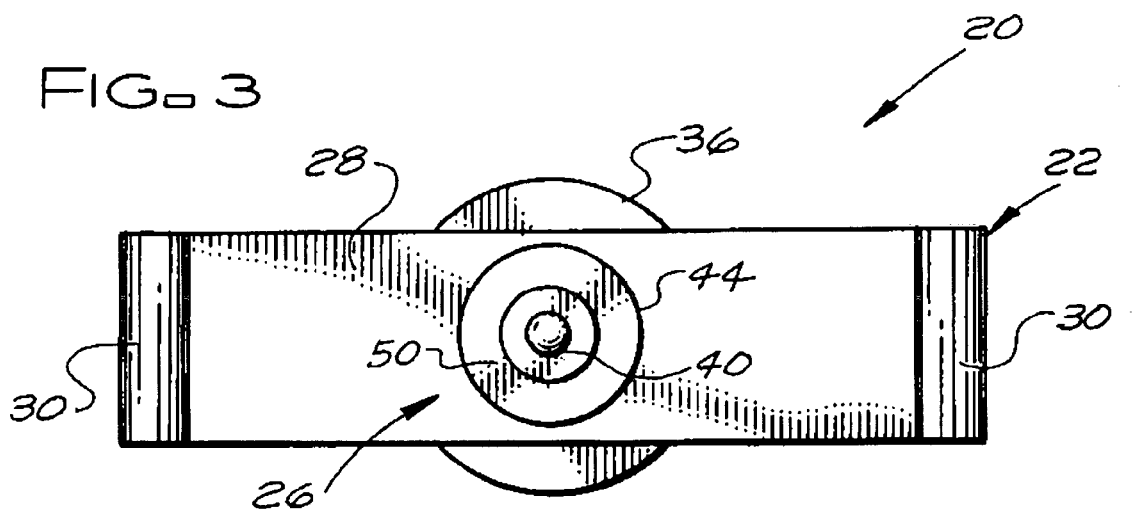
FIG. 3 is a front view of the portable gauge of FIG. 1.

The portable gauge 20 of the subject invention shown in FIGS. 1 to 3 includes a frame 22, a spring-loaded plunger assembly 24, and a readout assembly 26. The frame 22 of the portable gauge 20 has a rigid cross member 28 that is formed by a rigid plate. The rigid cross member 28 has a width "W" greater than the cavity width of the building cavities with which the portable gauge 20 will be used so that the cross member 28 of the frame 22 will overlap the front faces of the framing members forming the sidewalls of the cavities being tested (e.g. for building cavities formed by framing members on 16 inch centers a width of at least 16 inches and for building cavities formed by framing members on 24 inch centers a width of at least 24 inches). The frame 22 also includes handles 30 that can be used to carry the portable gauge 20 and press the rear side of the frame cross member 28 against the front faces of the framing members forming the sidewalls of the cavity being tested with the portable gauge 20.

As shown in FIGS. 1 to 3, the plunger assembly 24 includes a plunger 32 and a coil spring 34. The plunger assembly 24 is mounted on the cross member 28 of the frame 22, preferably, midway or about midway between the ends of the cross member 28 so that the plunger assembly 24 will normally be centered or substantially centered between the framing members forming the sidewalls of a cavity being tested with the portable gauge 20. The plunger 32 of the plunger assembly 24 includes a plunger faceplate 36 and a plunger stem 38. The plunger faceplate 36 has a predetermined surface area for compressing that predetermined surface area of a loose-fill insulation within a cavity to a compressed density greater than the as installed density of the loose-fill insulation and to a compressed thickness less than the as installed thickness of the loose-fill insulation. While, as shown, the faceplate 36 is circular in shape, the faceplate 36 could have other shapes, such as but not limited to square, rectangular, or oval.

The plunger stem 38 extends from the plunger faceplate 36 through the cross member 28 and the readout assembly 26 and has a free end that extends beyond the readout assembly 26. The plunger stem 38 is slideably mounted in the cross member 28 and the readout assembly 26 so that the plunger stem 38, and thus the plunger 32, can move to-and-fro relative to the frame 22 and the readout assembly 26. The coil spring 34 surrounds the plunger stem 38 and extends between the faceplate 36 and the rear side of the cross member 28. The coil spring 34 urges the plunger 32 of the plunger assembly 24 away from the rear side of the frame 22 and the free end of the plunger stem has a stop 40 thereon which cooperates with the readout assembly 26 to retain the plunger in the portable gauge. Preferably, the plunger stem 38 has a length that enables the plunger faceplate 36 to be extended by the action of the coil spring 34 a distance, away from the rear side of the cross member 28 and toward the rear surface of the cavity being tested, at least equal to or substantially equal to or greater than the depth of the building cavities to be tested with the portable gauge 20 to compress a portion of the loose-fill insulation within the cavity between the plunger faceplate and the rear surface of the cavity. Upon the application of the portable gauge 20 to the framing members of a cavity, the force exerted on the plunger 32 by the spring 34 or other force producing mechanism and by the plunger faceplate 36 on the loose-fill insulation between the plunger faceplate and the rear surface of the cavity is sufficient to compress the loose-fill insulation from its as installed thickness to a lesser thickness and to compress the loose-fill insulation from its as installed density to a greater density which is sufficiently dense or compact that further compressive movement of the plunger (plunger creep) is stopped or substantially stopped. Preferably, the compressive movement of the plunger 32 caused by the spring 34 or other force producing mechanism and by the plunger faceplate 36 on the loose-fill insulation between the plunger faceplate and the rear surface of the cavity is rapid and quickly compresses the loose-fill insulation from its as installed thickness to the lesser thickness and from its as installed density to the density that stops or substantially stops further compressive movement of the plunger (plunger creep).

The different types of loose-fill insulation typically installed in building cavities may be installed at densities that lie within different density ranges and may have different compressive properties so that these different loose-fill insulations compress to different degrees under a given force. For example, loose-fill fiberglass based insulations, as installed in a building cavity, normally range in density between about 0.8 pcf and about 3 pcf (pounds per cubic foot); loose-fill cellulose fiber based insulations, as installed in a building cavity, normally range in density between about 2 pcf and about 4 pcf; loose-fill rock wool based insulations, as installed in a building cavity, normally range in density between about 3 pcf and about 6 pcf; and other loose-fill insulation could have as installed density ranges where the higher end of the range is greater than 6 pcf. Furthermore, these different types of loose-fill insulations may be installed without adhesives or as an admixture of the insulation and one or more adhesives at various concentrations. As a result of possible different compressive and/or other physical properties for different loose-fill insulations, while the portable gauge 20 may be calibrated for different loose-fill insulations having the same physical properties, the portable gauge 20 is normally calibrated for a particular loose-fill insulation. For a particular loose-fill insulation, a particular as installed loose-fill insulation thickness (e.g. normally the cavity depth), and a particular cavity depth, the compressed thickness of the particular loose-fill insulation between the plunger faceplate 36 of a particular portable gauge 20 and the rear surfaces of cavities of the particular depth: depends on the as installed density of the particular loose-fill insulation; will vary for different as installed densities of the particular loose-fill insulation; and will be the same for the same as installed density of the particular loose-fill insulation. For a particular loose-fill insulation, the compressed thicknesses of the loose-fill insulation for different as installed densities are correlated (typically through testing) to the as installed density of the loose-fill insulation; the as installed density of the loose-fill insulation is then correlated (typically through testing) to one or more as installed thermal, acoustical and/or other density related properties of the loose-fill insulation to calibrate the portable gauge; and the portable gauge is provided with a scale or scales with calibrated markings, such as but not limited to bands, that provide the installer with easy to read accurate and reliable values for the density related property or properties of the as installed loose-fill insulation.

The readout assembly 26 of the portable gauge 20 can be permanently calibrated for a particular loose-fill insulation (e.g. a fiberglass based insulation, a cellulose fiber based insulation, a rock wool fiber based insulation, or other loose-fill insulation) or where applicable, for two or more loose-fill insulations having substantially the same physical properties, for a particular as installed insulation thickness (e.g. normally the cavity depth), and for a particular cavity depth (e.g. in the United States approximately a 3.5 inch, 5.5 inch, 7.25 inch and 9.25 inch cavity depth. However, in preferred embodiments of the invention, the readout assembly 26 of the portable gauge 20 can be adjusted to calibrate the readout assembly for different loose-fill insulations, different as installed insulation thicknesses, and/or different cavity depths.

The following is an example of a procedure that has been used to accurately calibrate the portable gauge 20.

Initial Calibration Procedure:
1. Apply loose-fill insulation in a framed cavity and remove excess insulation so that the insulation in the cavity is flush with the exposed faces of the framing members.
2. Push the portable gauge 20 into the cavity until the frame of the gauge makes contact with the exposed faces of the framing members. The plunger 32 of the portable gauge 20 will compress a portion of the insulation in the cavity by an amount proportional to the installed density of the insulation.
3. Read an inch scale on the plunger stem 38 of the portable gauge 20 to determine the amount of compression that has occurred and record the reading.
4. Remove a cylindrical core of the insulation from the circular area previously compacted by the plunger 32 with the portable gauge 20 using a cutter of a motorized hole saw attachment and positioning jig.
5. Carefully collect and weigh the cut core material to the nearest one thousandth of a pound.
6. Using the average inside diameter of the cutter along with the known cavity depth, calculate the volume of the insulation material contained in the removed core. Using the core weight and the volume of the core, calculate the installed density of the insulation.
7. Repeat steps 1 to 6 several times with various installed densities to cover the entire expected range of installed insulation density for the product.
8. Plot the calculated density and the portable gauge 20 measurements and establish a correlation equation. Use this equation to create a scale on the plunger stem 38 of the portable gauge 20 with density measurement increments in place of the inch scaling.
9. If desired, use an established relationship between R-value and density (usually from a known product thermal curve equation) and/or an established relationship between some other performance characteristic and density (usually from a known product performance curve equation such as an acoustical performance curve equation) to create a scale on the plunger stem 38 of the portable gauge 20 with R-value and/or some other performance measurement increments in place of the inch scaling.

Field Calibration:
1. Standardized gauge blocks of know thickness can be developed from the gauge readings versus density relationship. These gauge blocks will correspond to specific installed densities, R-values, or other performance values.
2. By placing a gauge block in an empty cavity and then pushing the portable gauge 20 onto the block until the frame of the portable gauge makes contact with the exposed faces of the faming members of the cavity, the desired density reading, R-value reading, or other performance value reading can be checked for accuracy.
3. If an exact desired reading is not obtained, the calibration cap 44 can be adjusted until the correct reading is obtained. The portable gauge 20 is then ready for installed insulation measurement.

One preferred embodiment of the readout assembly 26 of the portable gauge 20 includes a tubular housing 42, a calibration cap 44, and a lock nut 46. The tubular housing 42 and the calibration cap 44 are threaded together so that the calibration cap 44 can be adjusted relative to the housing 42 by being moved back and forth relative to the housing 42 in the direction of the longitudinal axis of the plunger stem 38 and a central axis of the housing 42. The lock nut 46 is used to lock the calibration cap 44 in place once the calibration cap has been adjusted to calibrate the portable gauge 20 for a particular loose-fill insulation, a particular as installed insulation thickness (e.g. normally the cavity depth), and a particular cavity depth. The plunger stem 38 of the plunger 32 is slideably received within and passes from the rear side of the gauge frame 22 through the frame, the tubular housing 42, and the calibration cap 44. The plunger stem 38 has a scale or scales 48 with graduated markings, such as but not limited to bands, on a portion of its free end that, with the calibration cap 44 properly adjusted, functions with the front face (exposed face) 50 of the calibration cap 44 to indicate a value or values for one or more as installed loose-fill insulation properties based on the as installed density of the loose-fill insulation within a cavity being tested. The desired as installed physical property or properties of the loose-fill insulation (e.g. density or thermal, acoustical, or other density related property) can then be easily determined by reading the appropriate graduated marking or markings of the scale(s) 48 on the plunger stem 38 relative to the front face 50 of the calibration cap 44. Where the graduated markings are or include bands, the bands can be used to indicate ranges over which the as installed loose-fill insulation falls within a property value, e.g. within an R-value for thermal performance.

Figure 6:
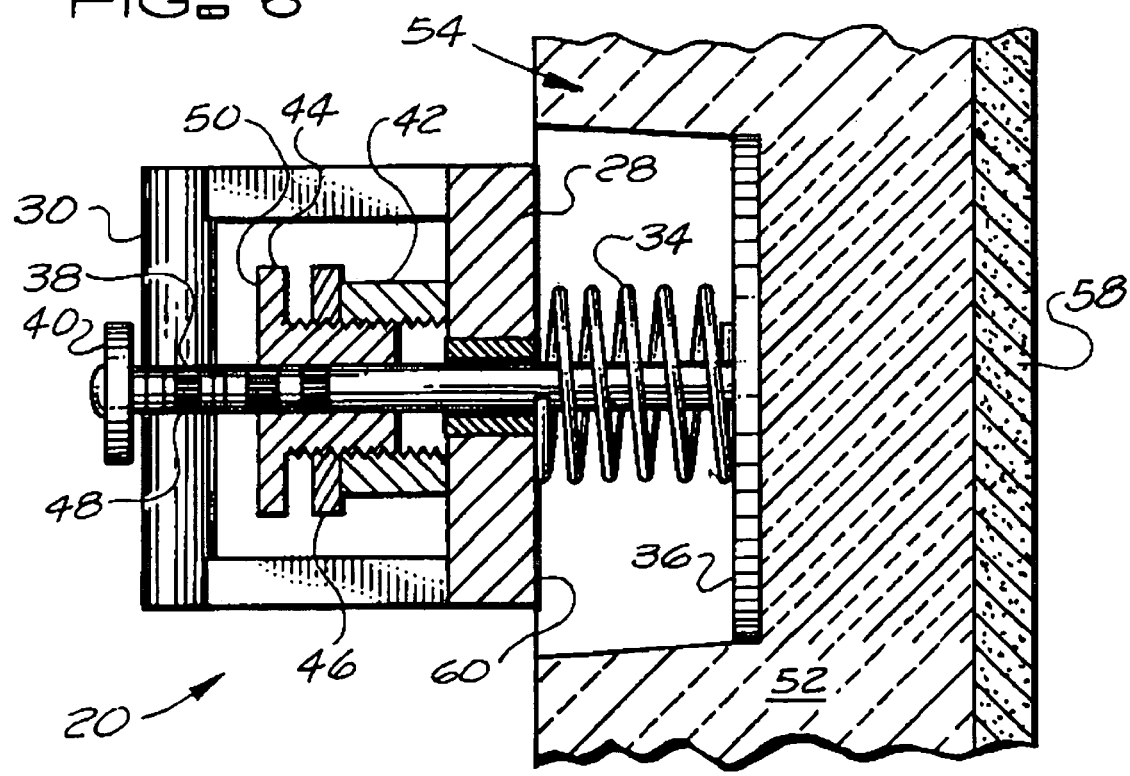
FIG. 6 is a vertical cross section through the open-front building cavity of FIG. 5, taken substantially along lines 6-6 of FIG. 5, with the portable gauge of FIGS. 1 to 3 being used to indicate an as installed density and/or other as installed density related property value of the loose-fill insulation within the cavity.
Figure 5:
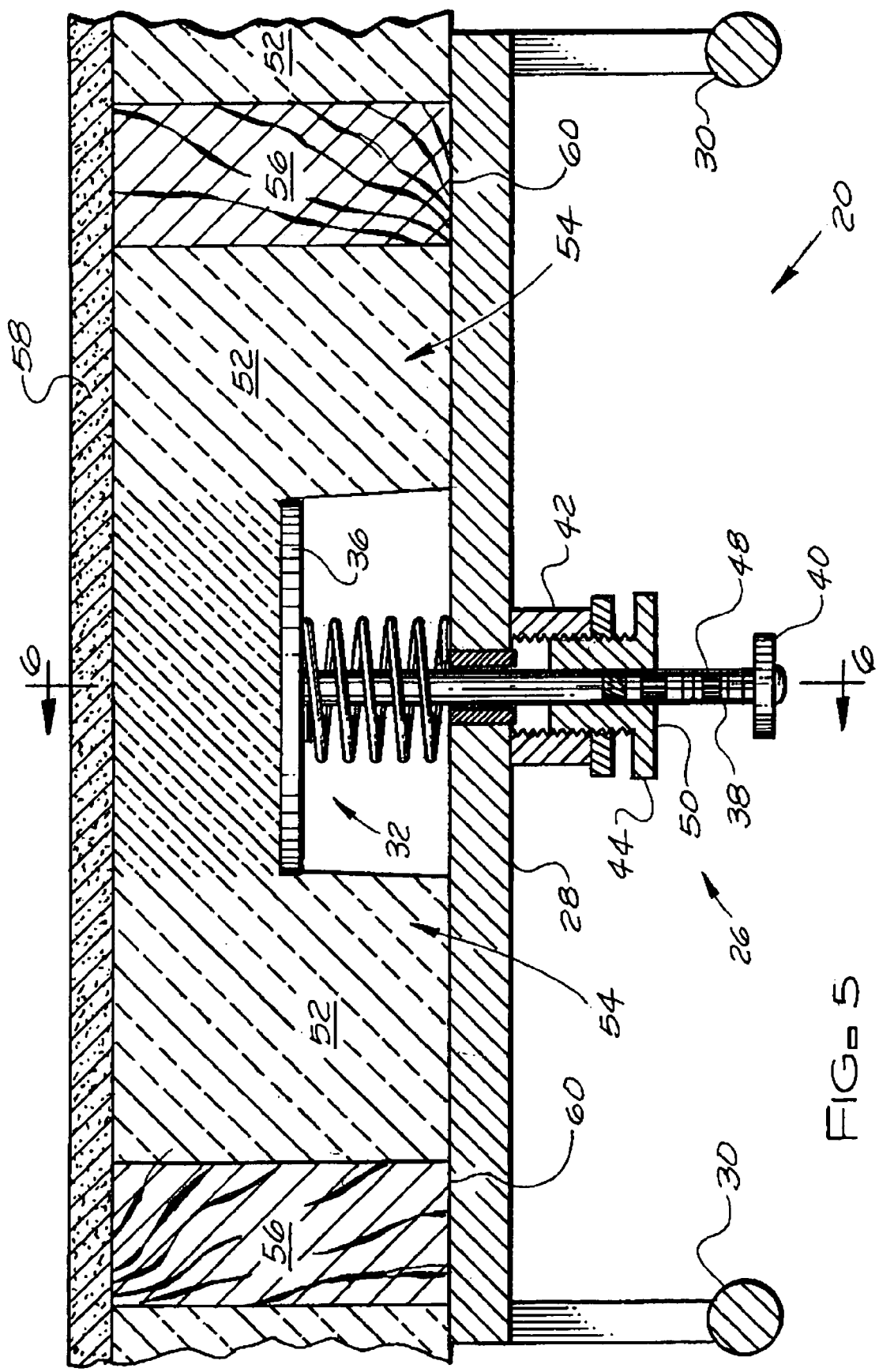
FIG. 5 is a horizontal cross section through an open-front building cavity with the portable gauge of FIGS. 1 to 3 being used to indicate an as installed density and/or other as installed density related property value of the loose-fill insulation within the cavity.

With the portable gauge 20 calibrated for a particular loose-fill insulation 52, a particular as installed insulation thickness which is normally the cavity depth, and a particular cavity depth, the portable gauge 20 can be used, as shown in FIGS. 5 and 6, to easily determine the as installed density and/or other as installed density related property of the loose-fill insulation 52 in such an open-front cavity 54. The open-front cavity 54 has sidewalls defined by the opposing surfaces of framing members 56, a rear surface formed by sheathing 58, and an open-front defined by a plane that also contains the front faces 60 of the framing members 56. As shown in FIGS. 5 and 6, the loose-fill insulation 52 has been installed in the open-front cavity 54 in accordance with normal industry standards with the front (exposed) surface of the loose-fill insulation 52 lying in or substantially lying in the plane of the open-front of the cavity 54 which is defined by the plane that contains the front faces 60 of the framing members 56.

With the frame cross member 28 of the portable gauge 20 held against the front faces 60 of the framing members 56 of the cavity 54 as shown in FIGS. 5 and 6, the degree to which the plunger faceplate 36 penetrates into the cavity 54 compressing the loose-fill insulation 52 between the faceplate 36 and the rear surface 62 of the cavity formed by the sheathing 58 relates to the as installed density of the loose-fill insulation 52 being compressed within the cavity and determines the degree to which the free end 64 of the plunger stem 38 extends beyond the exposed face 50 of the calibration cap 44. In other words, the greater the as installed density of the loose-fill insulation 52 being compressed by the portable gauge 20 within the cavity 54, the less distance the plunger assembly faceplate 36 will penetrate into the cavity 54 before the compression of the loose-fill insulation 52 by the plunger stops and the more the plunger assembly stem 38 will extend beyond the front face 50 of the calibration cap 44 which functions as an indicator to indicate the as installed density and/or other as installed density related property value of the loose fill insulation 52 (e.g. an as installed R-value for the insulation). As mentioned above, the plunger stem 38 has a scale or scales 48 with graduated markings on a portion of its free end that, with the calibration cap 44 properly adjusted, functions with the front face (exposed face) 50 of the calibration cap 44 to indicate a value or values for one or more as installed loose-fill insulation properties based on the as installed density of the loose-fill insulation 52 within the building cavity 54 being tested. The desired as installed physical property or properties of the loose-fill insulation 52 (e.g. density or thermal, acoustical, or other density related property) can then be easily determined by reading the appropriate graduated markings of the scale(s) 48 on the plunger stem 38 relative to the front face 50 of the calibration cap 44.

Figure 4:
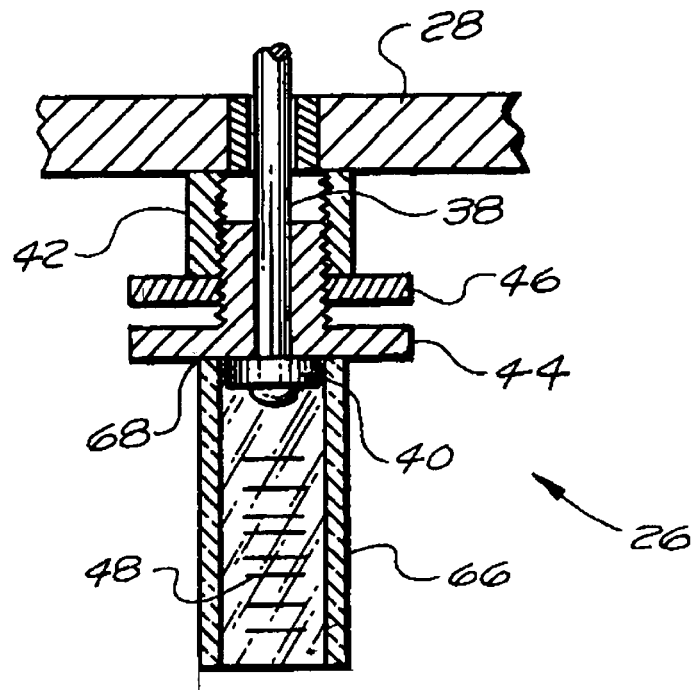
FIG. 4 is a horizontal cross section through an alternative structure for the readout assembly of the portable gauge of the subject invention.

With regard to the readout assembly 26, it is also contemplated that, as shown in FIG. 4, the scale(s) 48 could be located on a transparent tubular extension 66 of the calibration cap 44 and the stop 40 at the free end of the plunger stem could function as the indicator for indicating the as installed density and/or the other as installed density related property of the loose-fill insulation 52. The stop 40 would be slideably received within the transparent tubular extension 66 and cooperates with the rear end 68 of the tubular extension 66 to retain the plunger 32 in the portable gauge 20.

In describing the invention, certain embodiments have been used to illustrate the invention and the practices thereof. However, the invention is not limited to these specific embodiments as other embodiments and modifications within the spirit of the invention will readily occur to those skilled in the art on reading this specification. Thus, the invention is not intended to be limited to the specific embodiments disclosed, but is to be limited only by the claims appended hereto.

What is claimed is:

1. A portable gauge for indicating an as installed property of a loose-fill insulation in a building cavity wherein the cavity has a given depth, an open front, a rear surface, and sidewalls defined by spaced apart framing members and the framing members have front surfaces that lie in a common plane with the open front of the cavity; the portable gauge, comprising:

a rigid frame for extending between and overlapping the front surfaces of the framing members defining the sidewalls of the cavity so that the frame can be held against the front surfaces of the framing members defining the sidewalls of the cavity; the rigid frame having a front side and a rear side;

a plunger assembly mounted on the rigid frame; the plunger assembly having a plunger that includes a plunger faceplate and a plunger stem with the plunger faceplate being on the rear side of the frame; the plunger being mounted on the frame for to-and-fro motion substantially equal to or greater than the depth of the cavity; the plunger assembly having a force generating mechanism for urging the plunger faceplate away from the rear side of the frame with sufficient force to compress a portion of a loose-fill insulation, located in the cavity between the plunger faceplate and the rear surface of the cavity, to a compressed thickness less than the as installed thickness of the loose-fill insulation in the cavity and to a compressed density, greater than the as installed density of the loose-fill insulation in the cavity, that is sufficiently dense to substantially stop further movement of the plunger by the force generating mechanism; and a readout means calibrated to indicate an as installed property of the loose-fill insulation within the cavity for a given as installed thickness of the loose-fill insulation; the readout means being calibrated to indicate the as installed property of the loose-fill insulation by correlating the compressed thickness the loose-fill insulation, with the rear side of the gauge frame held against the front faces of the framing members defining the open front of the cavity, to the as installed property of the loose-fill insulation.

2. The portable gauge according to claim 1, wherein: the readout means is calibrated to indicate an as installed property of a loose-fill insulation within the cavity when the loose-fill insulation has an as installed thickness equal to or substantially equal to the depth of the cavity.

3. The portable gauge according to claim 1, wherein: the force generating mechanism for urging the plunger faceplate away from the rear side of the frame is a coil spring surrounding the plunger stem and extending between the frame and the plunger faceplate.

4. The portable gauge according to claim 3, wherein: the readout means includes an indicator and a calibrated member with graduated markings that, with the rear side of the frame held against the front faces of the framing members defining the open front of the cavity, are positioned relative to each other in response to the compressed thickness of the loose-fill insulation to indicate an as installed property of the loose-fill insulation.

5. The portable gauge according to claim 1, wherein: the readout means includes an indicator and a calibrated member with graduated markings that, with the rear side of the frame held against the front faces of the framing members defining the open front of the cavity, are positioned relative to each other in response to the compressed thickness of the loose-fill insulation to indicate an as installed property of the loose-fill insulation.

6. The portable gauge according to claim 5, wherein: the indicator is mounted on the front side of the frame; and a portion of the plunger stem is the calibrated member with graduated markings.

7. The portable gauge according to claim 5, wherein: the calibrated member with the graduated markings is mounted on and extends outward from the front side of the frame; and a free end of the plunger stem is the indicator.

8. The portable gauge according to claim 1, wherein: the readout means can be adjusted to calibrate the portable gauge for different loose-fill insulations, different as installed insulation thicknesses, and/or different cavity depths.

9. The portable gauge according to claim 8, wherein: the readout means includes a housing and a cap; the housing has a hollow central core for receiving the plunger stem and is mounted on the front side of the frame; the cap is adjustably mounted relative to the housing so that the cap can be moved to-and-fro relative to the housing in a direction coinciding with a longitudinal axis of the plunger stem; a portion of the plunger stem has graduated markings thereon to indicate an as installed property of the loose-fill insulation; and the plunger stem passes through the frame, the housing, and the cap with the portion of the plunger stem having the graduated markings extending through the cap whereby a front surface of the cap forms the indicator and by adjusting the cap relative to the housing, the portable gauge can be calibrated for different loose-fill insulations, different as installed loose-fill insulation thicknesses, and/or different cavity depths.

10. The portable gauge according to claim 9, wherein: the as installed property of the loose-fill insulation indicated by the readout means is an as installed density and/or an as installed thermal or acoustical property of the loose-fill insulation.

11. A method for determining an as installed property of a loose-fill insulation in a building cavity wherein the cavity has a given depth, an open front, a rear surface, and sidewalls defined by spaced apart framing members and the framing members having front surfaces that lie in a common plane with the open front of the cavity, the method comprising:
introducing a loose-fill insulation into the cavity until a front surface of the loose-fill insulation lies in or substantially lies in the common plane containing the front surfaces of the framing members and the open front of the cavity;
utilizing the front surfaces of the framing members to position a portable gauge for indicating an as installed property of the loose-fill insulation in the cavity;
utilizing a compression means of the positioned portable gauge to compress a portion of the loose-fill insulation, located in the cavity between a faceplate of the compression means and the rear surface of the cavity, to a compressed thickness less than the as installed thickness of the loose-fill insulation and to a compressed density that is greater than the as installed density of the loose-fill insulation and sufficiently dense to substantially stop further compression of the loose-fill insulation by the compression means; and
utilizing the compressed thickness of the loose-fill insulation to indicate, with the portable gauge, an as installed property of the loose-fill insulation.

12. The method for determining an as installed property of a loose-fill insulation in a building cavity according to claim 11, wherein:
the portable gauge includes:
a rigid frame for extending between and overlapping the front surfaces of the framing members defining the sidewalls of the cavity so that the frame can be held against the front surfaces of the framing members defining the sidewalls of the cavity; the rigid frame having a front side and a rear side;
the compression means comprises a plunger assembly mounted on the rigid frame; the plunger assembly having a plunger that includes the faceplate and a plunger stem with the plunger faceplate being on the rear side of the frame; the plunger being mounted on the frame for to-and-fro motion substantially equal to or greater than the depth of the cavity; the plunger assembly having a force generating mechanism for urging the plunger faceplate away from the rear side of the frame with sufficient force to compress the portion of the loose-fill insulation, located in the cavity between the plunger faceplate and the rear surface of the cavity, to the compressed thickness and density; and
readout means calibrated to indicate an as installed property of the loose-fill insulation within the cavity; the readout means being calibrated to indicate the as installed property of the loose-fill insulation by correlating the compressed thickness the loose-fill insulation, with the rear side of the gauge frame held against the front faces of the framing members defining the open front of the cavity, to the as installed property of the loose-fill insulation.

13. The method for determining an as-installed property of a loose-fill insulation according to claim 12, wherein:
the force generating mechanism for urging the plunger faceplate away from the rear side of the frame is a coil spring surrounding the plunger stem and extending between the frame and the plunger faceplate.

14. The method for determining an as installed property of a loose-fill insulation in a building cavity according to claim 13, wherein:
the readout means includes an indicator and a calibrated member with graduated markings that, with the rear side of the frame held against the front faces of the framing members defining the open front of the cavity, are positioned relative to each other in response to the compressed thickness of the loose-fill insulation to indicate an as installed property of the loose-fill insulation.

15. The method for determining an as installed property of a loose-fill insulation in a building cavity according to claim 12, wherein:
the readout means includes an indicator and a calibrated member with graduated markings that, with the rear side of the frame held against the front faces of the framing members defining the open front of the cavity, are positioned relative to each other in response to the compressed thickness of the loose-fill insulation to indicate an as installed property of the loose-fill insulation.

16. The method for determining an as installed property of a loose-fill insulation in a building cavity according to claim 15, wherein:
the indicator is mounted on the front side of the frame; and a portion of the plunger stem is the calibrated member with graduated markings.

17. The method for determining an as installed property of a loose-fill insulation in a building cavity according to claim 15, wherein:
the calibrated member with the graduated markings is mounted on and extends outward from the front side of the frame; and a free end of the plunger stem is the indicator.

18. The method for determining an as installed property of a loose-fill insulation in a building cavity according to claim 12, wherein:
the readout means can be adjusted to calibrate the portable gauge for different loose-fill insulations, for different as installed loose-fill insulation thicknesses, and/or different cavity depths.

19. The method for determining an as installed property of a loose-fill insulation in a building cavity according to claim 18, wherein:
the readout means includes a housing and a cap; the housing has a hollow central core for receiving the plunger stem and is mounted on the front side of the frame; the cap is adjustably mounted relative to the housing so that the cap can be moved to-and-fro relative to the housing in a direction that coincides with a longitudinal axis of the plunger stem; a portion of the plunger stem has graduated markings thereon to indicate an as installed property of the loose-fill insulation; and the plunger stem passes through the frame, the housing, and the cap with the portion of the plunger stem having the graduated markings extending through the cap whereby a front surface of the cap forms the indicator and by adjusting the cap relative to the housing, the portable gauge can be calibrated for different loose-fill insulations, different as installed loose-fill insulation thicknesses, and/or different cavity depths.

20. The method for determining an as installed property of a loose-fill insulation in a building cavity according to claim 19, wherein:
the as installed property of the loose-fill insulation indicated by the readout means is an as installed density and/or an as installed thermal or acoustical property of the loose-fill insulation.

\* \* \* \* \*